United States Patent [19]

Rozsa et al.

[11] Patent Number: 4,906,622
[45] Date of Patent: Mar. 6, 1990

[54] OPTICALLY ACTIVE 2-CHLORO-12-(3-DIMETHYLAMINO-2-METHYL-PROPYL)-12H-DIBENZO[D.G][1,3,6] DIOXAZOCINES AND A PROCESS FOR THE PREPARATION THEREOF

[75] Inventors: Laszlo Rozsa; Lujza Petöcz; Enikö Szirt nee Kiszelly; Peter Tömpe; Gabor Gigler, all of Budapest, Hungary

[73] Assignee: Egis Gyogyszergyar, Budapest, Hungary

[21] Appl. No.: 195,691

[22] Filed: May 18, 1988

Related U.S. Application Data

[63] Continuation-in-part of Ser. No. 921,672, Oct. 21, 1986, abandoned.

[30] Foreign Application Priority Data

Dec. 20, 1985 [HU] Hungary ............................ 4881/85

[51] Int. Cl.⁴ ................ C07D 267/22; A61K 31/395
[52] U.S. Cl. .................................... 514/183; 540/468
[58] Field of Search ........................ 540/468; 514/183

[56] References Cited

U.S. PATENT DOCUMENTS 4,208,410 6/1980 Rozsa et al. ..................... 540/468

Primary Examiner—Richard L. Raymond
Assistant Examiner—Mark W. Russell
Attorney, Agent, or Firm—Herbert Dubno; Jonathan Myers

[57] ABSTRACT

The invention relates to optically active 2-chloro-12-(3-dimethylamino-2-methylpropyl)-12H-dibenzo[d,g][1,3,6]dioxazocine of the Formula

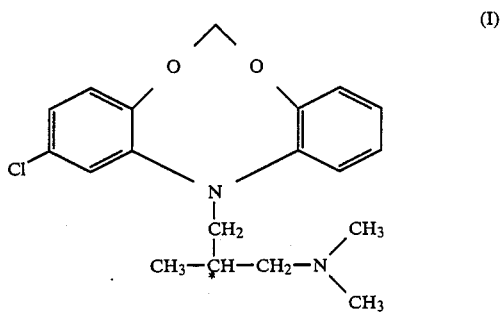

(I)

and pharmaceutically acceptable acid additional salts thereof. The enantiomers are especially active against Parkinson's disease.

The optically active enantiomers are prepared by
(a) resolving the racemic 2-chloro-12-(3-dimethylamino-2-methylpropyl)-12H-dibenzo[d,g][1,3,6]-dioxazocine with a optically active organic acid and separating the enantiomers; or
(b) dissolving the racemic 2-chloro-12-(3-dimethylamino-2-methylpropyl)-12H-dibenzo[d,g][1,3,6]-dioxazocine in an organic solvent, crystallizing and isolating one of the enantiomers, optionally dissolving additional racemic 2-chloro-12-(3-dimethylamino-2-methylpropyl)-12H-dibenzo[d,g][1,3,6]-dioxazocine in the mother liquor obtained and crystallizing and isolating the other enantiomer, and, if desired, repeating the whole process.

5 Claims, No Drawings

OPTICALLY ACTIVE 2-CHLORO-12-(3-DIMETHYLAMINO-2-METHYL-PROPYL)-12H-DIBENZO[D.G] [1,3,6] DIOXAZOCINES AND A PROCESS FOR THE PREPARATION THEREOF

CROSS REFERENCE TO RELATED APPLICATIONS

This application is a continuation-in-part of Ser. No. 921,672 filed 10-21-86, now abandoned.

The invention relates to novel optically active 2-chloro-12-(3-dimethylamino-2-methylpropyl)-12H-dibenzo[d,g][1,3,6]dioxazocines of the Formula I,

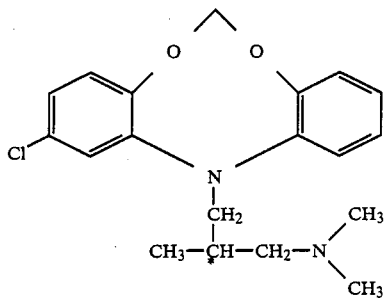

their preparation and compositions containing them. The novel optically active dioxazocines possess favorable pharmaceutical activity such as neuroleptic activity and are suitable especially for treating Parkinson's disease.

It is known that the racemic 2-chloro-12-(3-dimethylamino-2-methylpropyl)-12H-dibenzo[d,g][1,3,6]-dioxazocine has local anaesthetic and antiparkinsonic activity [U.S. Pat. No. 4,208,410]. The antiparkinsonic activity of this known compound was determined on a population of 500 mice, thus, rather exact results were obtained ($ED_{50}=11$ mg/kg; therapeutic index=25). The racemic compound possesses an asymmetric carbon atom, thus, two optically active isomers may exist. These isomers have not been separated yet.

It was found that the optically active compounds of the Formula I possess considerably higher antiparkinsonic activity than that of the racemic compound. This is supported by the following pharmaceutical test data.

The hydrochloride of the racemic compound, the hydrochloride of the (−)-isomer [compound of Example 6; the salt has (+) rotation] and the hydrochloride of the (+)-isomer [compound of Example 7; the salt has (−) rotation] were tested for acute toxicity on mice with peroral treatment and for the inhibition of tremor induced by tremorine (the latter test characterizes the action against Parkinson's disease). In the latter case, the inhibition of tremor induced by tremorine [1,1′-(2-butynylene)-dipyrrolidine] administered intraperitoneally at a dosage of 20 mg/kg was tested on mice as described in Science, 124, 79 (1956). The compound to be examined was given perorally to a population of 50 mice one hour prior to the administration of tremorine, and the tremor developed was evaluated 45 minutes after the administration of tremorine. The results obtained are shown in Table 1.

From Table 1 it can be seen that although the therapeutical index of the racemic compound is equivalent to 10.8, that of the antipodes is higher by a factor of 6 to 7. This fact is surprising since, in general, one of the antipodes has higher and the other one has lower activity than that of the racemic compound.

TABLE 1

| | Inhibition of tremor induced by tremorine | | |
|---|---|---|---|
| Compound | $LD_{50}$ (mg/kg) p.o. | $ED_{50}$ (mg/kg) p.o. | T.I. |
| racemic | 270 | 25 | 10.8 |
| 6 | 160 | 2.2 | 72.7 |
| 7 | 460 | 7 | 65.7 |

T.I. = therapeutic index

Since a lower population of mice was used, less exact values of $ED_{50}$ were obtained for the compounds tested. Thus, the therapeutic index calculated for the racemic compound is lower by a factor of about 2.4 than the value given in U.S. Pat. No. 4 4,208,410. However, the data obtained under identical test circumstances on a relatively low number of test animals can be compared with each other.

To make sure that no contradiction exists between the data of Table I on the one hand, and the data of U.S. Pat. No. 4,208,410 on the other hand, the above tests was repeated using a population of 500 mice for each compound tested. The results obtained are given in Table 2.

TABLE 2

| Compound (Example No.) | $LD_{50}$ (mg/kg) p.o. | $ED_{50}$ (mg/kg) p.o. | T.I. |
|---|---|---|---|
| racemic | 270 | 10.5 | 25.7 |
| 6 | 160 | 0.95 | 168.4 |
| 7 | 460 | 2.86 | 160.8 |

The data of Table 2 confirm that both antipodes have much higher antiparkinsonic activity than that of the racemic compound.

Although the primary tests indicates that the racemic compound has local anaesthetic activity, detailed tests have not shown any therapeutically valuable effect. Accordingly, it was found that none of the antipodes has this activity.

The optically active compounds of the Formula I can be prepared from the racemic 2-chloro-12-(3-dimethylamino-2-methylpropyl)-12H-dibenzo-[d,g][1,3,6]-dioxazocine through the separation of the enantiomers.

According to one process variant of the invention, the racemic compound is resolved with an optically active organic acid. In the specification, the term "resolution" refers to a process comprising the following steps:

(i) one of the antipodes or both of them is/are converted to an acid addition salt by means of an optically active organic acid;

(ii) the salt of one antipode with the optically active organic acid is separated from the other antipode or the salt thereof formed with the optically active organic acid through crystallization from a suitable solvent;

(iii) one of the antipodes or reach of them is/are deliberated from the acid addition salt and isolated.

As an optically active organic acid practically any carboxylic acid used for resolutions can be employed such as atrolactic acid, tartaric acid, dibenzoyltartaric acid, hydrotropic acid, mandelic acid, 2-pyrrolidone-5-carboxylic acid, lactic acid, substituted lactic acids; amino acids or derivatives thereof e.g. asparagine, glutamic acid, leucine, N-acetylleucine, N-(p-toluenesulfonyl)-glutamic acid etc.; furthermore optically active sulfonic acids such as 10-camphorsulfonic acid, 6,6'-dinitro-2,2'-diphenic acid etc.

It is preferred to resolve the racemic 2-chloro-12-(3-dimethylamino-2-methylpropyl)-12H-dibenzo[d,g]-[1,3,6]dioxazocine with L-(+)-tartaric acid.

In the resolution of the invention, the optically active organic acid can be employed in molar equivalent amount to the racemic base. Alternatively, both higher and lower amounts of the optically active organic acid can be used.

As a suitable solvent water; polar, apolar or dipolar organic solvents such as an aromatic hydrocarbon, e.g. benzene, toluene or xylene; a halogenated aliphatic or aromatic hydrocarbon, e.g. dichloromethane, 1,2-dichloroethane, chloroform, carbon tetrachloride or chlorobenzene; an alkanol e.g. methanol, ethanol, isopropanol or dodecanol; dimethyl formamide; dimethyl sulfoxide; acetonitrile etc. or mixtures thereof can be employed.

It is preferred to resolve the racemic dioxazocine compound in an aqueous medium or in dichloromethane.

The resolution of the invention is performed, in general, at a temperature from about 0° C. to about 100° C.

According to a further process variant of the invention, the antipodes are separated by physical resolution on the basis of their solubility being different from that of the racemic compound. Thus, the racemic compound is dissolved in a suitable organic solvent and the solution obtained is seeded with one of the pure enantiomers to crystallize the same enantiomer. In this way, a higher quantity of this enantiomer can be isolated.

If the other enantiomer is to be isolated, too, a further amount of the racemic compound is dissolved in the mother liquor—preferably, the original concentration of the racemic compound is resorted—and the solution obtained is seeded with the other pure enantiomer to crystallize the same enantiomer.

The above process can be repeated practically any number of times, thus, in theory, an infinite number of resolution cycles can be carried out.

In the physical resolution process of the invention, the solvent can be a polar or apolar organic solvent such as an alcohol e.g. methanol, ethanol, propanol, butanol etc.; or a hydrocarbon e.g. benzene, toluene, xylene, petroleum ether etc.; or a mixture thereof. The preferred solvent is isopropanol.

The temperature of the physical resolution of the invention is, in general, 0° to 100° C., preferably 15° to 45° C.

If desired, the optically active dixoazocines of the invention are reacted with an inorganic or organic acid to give a pharmaceutically acceptable acid addition salt. During the salt formation, it may occur that a base having (+) rotation gives an acid addition salt having (−) rotation, and conversely, a base having (−) rotation can give an acid addition salt of (+) rotation.

Thus, in accordance with the invention, one proceeds as follows:
 (a) racemic 2-chloro-12-(3-dimethylamino-2-methylpropyl)-12H-dibenzo[d,g][1,3,6]dioxazocine is resolved with an optically active organic acid and the enantiomers are separated; or
 (b) racemic 2-chloro-12-(3-dimethylamino-2-methylpropyl)-12H-dibenzo-[d,g][1,3,6]dioxazocine is dissolved in an organic solvent and one of the enantiomers is crystallized and isolated, optionally additional racemic dioxazocine is dissolved in the mother liquor obtained and the other enantiomer is crystallized and isolated, and, if desired, the whole process is repeated;
 and, if desired, an enantiomer obtained is converted to an acid addition salt with an inorganic or organic acid.

The invention refers to pharmaceutical compositions, especially for treating Parkinson's disease. Such pharmaceutical compositions comprise 2-chloro-12-(3-dimethyl-amino-2-methylpropyl)-12H-dibenzo[d,g][1,3,6]dioxazocine in optically active form or a pharmaceutically acceptable acid addition salt thereof and one or more pharmaceutical carrier(s).

The pharmaceutical composition of the invention is prepared by admixing an optically active 2-chloro-12-(3-dimethylamino-2-methylpropyl)-12H-dibenzo[d,g][1,3,6]dioxazocine or a pharmaceutically acceptable acid addition salt thereof to one or more pharmaceutical carrier(s) and transforming the mixture obtained into a pharmaceutical composition.

The pharmaceutical composition of the invention is preferably administered orally or intraperitoneally. In the first place, capsules, tablets, dragees, suspensions, emulsions or solutions are given orally, and sterile solutions are injected intraperitoneally. The daily dose for an average adult is, in general, 0.1 to 1000 mg/kg, preferably 1 to 100 mg/kg.

Although the pharmaceutical composition of the invention is especially active against Parkinson's disease, due to the neuroleptic activity of the optically active compounds of the Formula I, the composition can be employed as a tranquilizer, too.

The invention is further elucidated by means of the following Examples.

EXAMPLE 1

(−)-2-Chloro-12-(3-dimethylamino-2-methylpropyl)-12H-dibenzo[d,g][1,3,6]dioxazocine (A) 34.7 g (0.1 moles) of racemic 2-chloro-12-(3-dimethylamino-2-methylpropyl)-12H-dibenzo[d,g][1,3,6]-dioxazocine and 16.5 g (0.11 moles) of L(+)-tartaric acid are suspended in 120 cm$^3$ of water, and the suspension is stirred at room temperature. After one hour, a solution is obtained from which (−)-base L(+)-tartrate is precipitated in some hours. (The term "base" corresponds to the above dioxazocine compound in the basic form.) The crystals are filtered and dried. 19.8 g (79.2%) of (−)-2-chloro-(3-dimethylamino-2-methylpropyl)-12H-dibenzo[d,g][1,3,6]-dioxazocine L(+)-tartrate are obtained, m.p.: 110°–115° C.

$[\alpha]_D^{20} = +42.0°$ ($c=1$; water).

(B) To a stirred mixture of 19.0 g (0.038 moles) of (−)-2-chloro-12-(3-dimethylamino-2-methylpropyl)-12H-dibenzo[d,g][1,3,6]dioxazocine L(+)-tartrate, 100 cm$^3$ of water and 100 cm$^3$ of dichloromethane 25 percent aqueous ammonia is added until a pH value of 10. The mixture is stirred for further 30 minutes, the organic phase is separated and the solvent is removed under reduced pressure. The viscous residue is dissolved in 28 cm$^3$ of isopropanol, cooled to 0° C. and the crystals are filtered. 11.1 g 84.0% of the title compound are obtained, m.p.: 92°–95° C.

$[\alpha]_D^{20} = +95.4°$ ($c=5$; chloroform).

EXAMPLE 2

(−)-2-Chloro-12-(3-dimethylamino-2-methylpropyl)-12H-dibenzo[d,g][1,3,6]dioxazocine (A) To the filtrate obtained in Example 1, section A and having a volume of 110 to 120 cm³, 100 cm³ of dichloromethane are added and the base is deliberated as described in Example 1. To the dichloromethane solution containing 19.0 g of base as determined by means of titration with perchloric acid, an equivalent quantity of L(+)-tartaric acid is added under stirring. The mixture is stirred for several hours, the (+)-base L(+)-tartrate precipitated is filtered and dried. 21.6 g (87.0%) of (+)-2-chloro-12-(3-dimethylamino-2-methylpropyl)-12H-dibenzo[d,g][1,3,6]dioxazocine L(+)-tartrate are obtained, m.p.: 149°–152° C.

$[\alpha]_D^{20} = -28.2°$ (c=1; water).

(B) 19.0 g (0.038 moles) of (30)-2-chloro-12-(3-dimethylamino-2-methylpropyl)-12H-dibenzo[d,g][1,3,6]dioxazocine L(+)-tartrate are decomposed by the method described in Example 1, section (B). The title compound is obtained in a nearly theoretical yield. M.p.: 92°–95° C.

$[\alpha]_D^{20} = +95.3°$ (c=5; chloroform).

EXAMPLE 3

(+)-2-Chloro-12-(3-dimethylamino-2-methylpropyl)-12H-dibenzo[d,g][1,3,6]dioxazocine (A) 34.7 g (0.10 moles) of racemic 2-chloro-12-(3-dimethylamino-2-methylpropyl)-12H-dibenzo[d,g][1,3,6]dioxazocine are dissolved in 165 CM³ of dichloromethane, and 15.0 g (0.10 moles of L(+)-tartaric acid are added to the solution obtained under stirring. The mixture is further stirred for 10 to 12 hours at room temperature. The (+)-base L(+)-tartrate precipitated is filtered and dried. Thus, 15.8 g (63.7%) of (+)-2-Chloro-12-(3-dimethylamino-2-methylpropyl)-12H-dibenzo[d,g][1,3,6]dioxazocine L(+)-tartrate are obtained, m.p.: 148°–150° C.

$[\alpha]_D^{20} = -27.2°$ (c=1; water).

(B) (+)-2-Chloro-12-(3-dimethylamino-2-methylpropyl)-12H-dibenzo[d,g][1,3,6]dioxazocine L(+)-tartrate prepared as described above is decomposed by the method given in Example 1, section (B). The title compound is obtained in a nearly theoretical yield. M.p.: 93°–95° C.

$[\alpha]_D^{20} = +95.6°$ (c=6; chloroform).

EXAMPLE 4

(−)-2-Chloro-12-(3-dimethylamino-2-methylpropyl)-12H-dibenzo[d,g][1,3,6]dioxazocine (A) From the dichloromethane filtrate obtained in Example 3, section (A), the base is deliberated by the method of Example 1, section (B). To the residual syrup weighing 21.5 g, 9.3 g 0.063 moles of L(+)-tartaric acid are added in 85 CM³ of water. At first, a solution is obtained that is stirred for several hours. The (−)-base L(+)-tartrate precipitated is filtered, suspended in cold water, then filtered, suspended and filtered again. Thus, 17.5 g (70.0%) of (−)-2-chloro-12-(3-dimethylamino-2-methylpropyl)-12H-dibenzo[d,g][1,3,6]dioxazocine L(+)-tartrate are obtained, m.p.: 109°–114° C.

$[\alpha]_D^{20} = +41.2°$ C. (c=1; water).

(B) (−)-2-chloro-12-(3-dimethylamino-2-methylpropyl)-12H-dibenzo[d,g][1,3,6]dioxazocine L(+)-tartrate prepared as described above is decomposed by the method given in Example 1, section (B). The title compound is obtained in a nearly theoretical yield. M.p.: 92°–95° C.

$[\alpha]_D^{20} = -95.4°$ (c=5; chloroform).

EXAMPLE 5

(A) (−)-2-Chloro-12-(3-dimethylamino-2-methylpropyl)-12H-dibenzo[d,g][1,3,6]dioxazocine 138.8 g (0.40 moles) of racemic 2-chloro-12-(3-dimethyl-amino-2-methylpropyl)-12H-dibenzo[d,g][1,3,6]dioxazocine are dissolved in 1110 cm³ of isopropanol, and the solution is thermostated at 32±1° C. The concentration of the solution is determined and 14.0 g of (−)-enantiomer compound [m.p.: 93°–95° C.; $[\alpha]_D^{20} = -95.0$ (c=5; chloroform)] are added. The reaction mixture is stirred at the above temperature until the concentration of the liquid phase becomes lower by a 14.0 g of product. The crystals are filtered, washed with 20 cm³ of isopropanol at 0° C. and dried. 28.0 g of the title compound are obtained, m.p.: 93°–95 ° C.

$[\alpha]_D^{20} = 95.0°$ (c=5; chloroform).

(B) (+)-2-Chloro-12-(3-dimethylamino-2-methylpropyl)-12H-dibenzo[d,g][1,3,6]dioxazocine To the mother liquor obtained above, racemic-2-Chloro-12-(3-dimethylamino-2-methylpropyl)-12H-dibenzo[d,g][1,3,6]dioxazocine is added until the original concentration is restored. Then, the solution is again thermostated at 32±1° C. and 14.0 g of (+)-enantiomer compound [m.p.: 93°–95° C.; $[\alpha]_D^{20} = -95.0°$ (c=5; chloroform)] are added. Then, the process of Example 5, section (A) is followed. Thus, 28.0 g. of the title compound are obtained.

$[\alpha] = 95.0°$ (c=5; chloroform).

The process is repeated 17 times. After the seventeenth resolution cycle, 28.0 g of the (−)-enantiomer are obtained, m.p.: 92°–95° C.

$[\alpha]_D^{20} = -94.7°$ (c=5; chloroform).

After the eighteenth resolution cycle, 28.0 g of the (+)-enantiomer are obtained, m.p.: 92°–95° C., $[\alpha]_D^{20} = 94.5°$ (c=5; chloroform).

EXAMPLE 6

(+)-2-chloro-12-(3-dimethylamino-2-methylpropyl)-12H-dibenzo[d,g][1,3,6]dioxazocine hydrochloride 31.0 g (0.09 moles) of (−)-2-chloro-12-(3-dimethyl-amino-2-methylpropyl)-12H-dibenzo[d,g][1,3,6]dioxazocine are dissolved in 300 cm³ of anhydrous ether. To the solution cooled at 0° C., anhydrous ether containing hydrogen chloride is added under stirring until a pH value of about 3 is reached. The product precipitated is filtered, washed with anhydrous ether and recrystallized from isopropanol. Thus, 29.0 g (83.8%) of the title compound are obtained in the form of white crystals, m.p.: 183°–185° C. (dec.).

$[\alpha]_D = +53.5°$ ($c=3$; 0.1N hydrochloric acid).

Analysis for $C_{19}H_{24}Cl_2N_2O_2$ (383.33)

calculated: C 59.53%, H 6.31%, Cl 18.50%, N 7.31%, Cl⁻ 9.25%;

found: C 59.55%, H 6.26%, Cl 18.60%, N 7.35%, Cl⁻ 9.31%.

EXAMPLE 7

(−)-2-Chloro-12-(3-dimethylamino-2-methylpropyl)-12H-dibenzo[d,g][1,3,6]dioxazocine hydrochloride The process described in Example 6 is repeated, however, 31.0 g (0.09 moles) of (+)-2-Chloro-12-(3-dimethylamino-2-methylpropyl)-dibenzo[d,g][1,3,6]dioxazocine are employed. 28.3 g (82%) of the title compound are obtained, m.p.: 182°–185° C. (dec.).

$[\alpha]_D^{20} = -53.3°$ ($c=3$; 0.1N hydrochloric acid).

Analysis for $C_{19}H_{24}Cl_2N_2O_2$ calculated: C 59.53%, H 6.31%, Cl 18.50%, N 7.31%, Cl⁻ 9.25%;

found: C 59.80%, H 6.39%, Cl 18.59%, N 7.35%, Cl⁻ 9.33%.

We claim:

1. 2-Chloro-12-(3-dimethylamino-2-methylpropyl)-12H-dibenzo[d,g][1,3,6]dioxazocine in optically active form or a pharmaceutically acceptable acid addition salt thereof.

2. (+)-2-Chloro-12-(3-dimethylamino-2-methylpropyl)-12H-dibenzo[d,g][1,3,6]dioxazocine or a pharmaceutically acceptable acid addition salt thereof.

3. (−)-2-Chloro-12-(3-dimethylamino-2-methylpropyl)-12H-dibenzo[d,g][1,3,6]dioxazocine or a pharmaceutically acceptable acid addition salt thereof.

4. A pharmaceutical composition for treating Parkinson's disease comprising 2-chloro-12-(3-dimethylamino-2-methylpropyl)-12H-dibenzo[d,g][1,3,6]dioxazocine in optically active form or a pharmaceutically acceptable acid addition salt thereof and one or more pharmaceutical carrier(s).

5. A method of treating Parkinson's disease which comprises administering to a mammolian subject a therapeutically effective amount of an optically active 2-chloro-12-(3-dimethylamino-2-methylpropyl)-12H-dibenzo[d,g][1,3,6]dioxazocine or a pharmaceutically acceptable acid addition salt thereof.

* * * * *